United States Patent [19]

Starling et al.

[11] Patent Number: 4,839,215
[45] Date of Patent: Jun. 13, 1989

[54] BIOCOMPATIBLE PARTICLES AND CLOTH-LIKE ARTICLE MADE THEREFROM

[75] Inventors: L. Brian Starling, Golden; James E. Stephan, Arvada; William G. Hubbard, Lakewood, all of Colo.

[73] Assignee: Ceramed Corporation, Lakewood, Colo.

[21] Appl. No.: 872,617

[22] Filed: Jun. 9, 1986

[51] Int. Cl.$^4$ .................................................. B32B 3/10
[52] U.S. Cl. ..................................... 428/131; 428/137; 428/138; 428/283; 428/284; 428/323; 428/325; 428/327; 428/328; 428/402; 523/105; 523/114; 525/937
[58] Field of Search ............... 428/131, 137, 138, 402, 428/283, 323, 325, 327, 328, 284; 523/105, 114; 525/937; 604/49

[56] References Cited

U.S. PATENT DOCUMENTS

| | | | |
|---|---|---|---|
| 2,691,605 | 10/1954 | Hediger | 117/62 |
| 2,977,265 | 3/1961 | Forsberg et al. | |
| 3,066,233 | 11/1962 | Miller | |
| 3,276,448 | 10/1966 | Kronenthal | |
| 3,929,971 | 12/1975 | Roy | |
| 3,938,198 | 2/1976 | Kahn et al. | |
| 4,046,858 | 9/1977 | Barsa | |
| 4,075,092 | 2/1978 | White et al. | |
| 4,097,935 | 7/1978 | Jarcho | |
| 4,135,935 | 1/1979 | Pfeil et al. | |
| 4,149,893 | 4/1979 | Aoki et al. | |
| 4,193,137 | 3/1980 | Heck | |
| 4,195,409 | 4/1980 | Child | |
| 4,252,525 | 2/1981 | Child | |
| 4,255,820 | 3/1981 | Rothernel et al. | |
| 4,330,514 | 5/1982 | Nagai et al. | |
| 4,348,458 | 9/1982 | Otstot | 428/366 |
| 4,503,157 | 3/1985 | Hatahira | |

OTHER PUBLICATIONS

Erich Hayek and Heinrich Newesely, "Pentacalcium Monohydroxyorthophosphate," Inorganic Synthesis, vol. VII, 1963, pp. 63–65.
J. R. Narayanan Kutty, "Thermal Decomposition of Hydroxylapatite," Indian J. Chem., vol. 11, Jul. 1973, pp. 695–697.
Della M. Roy and Sari Kurtossy Linnehan, "Hydroxyapatite Formed from Coral Skeletal Carbonate by Hydrothermal Exchange," Nature, vol. 247, Jan. 25, 1974, pp. 220–222.
John N. Weber, Eugene W. White and Jana Lebiedzik, "New Porous Biomaterials by Replication of Echinoderm Skeletal Microstructures," Nature, vol. 233, Oct. 1, 1971, pp. 337–339.
E. A. Monroe, Ward Votava, D. B. Bass and James McMullen, "New Calcium Phosphate Ceramic Material for Bone and Tooth Implants," Journal of Dental Research, 1971, pp. 860–861.
Michael Jarcho, John F. Kay, Kenneth I. Gumaer, Robert H. Doremus and Hans P. Drobeck, "Tissue, Cellular and Subcellular Events at a Bone-Ceramic Hydroxylapatite Interface," Journal of Bioengineering, vol. I, pp. 79–92.

(List continued on next page.)

Primary Examiner—James J. Bell
Attorney, Agent, or Firm—Sheridan, Ross & McIntosh

[57] ABSTRACT

Biocompatible particles and an article incorporating a plurality of such particles is disclosed. The particles can have means for interconnecting such as an aperture for stringing the particles on a filament or interlocking external shape. A plurality of particles, with or without means for interconnecting, can be fashioned into an article by interconnecting the particles with a flexible material. When the particles have a means for interconnecting, the plurality of particles can also be interconnected by a rigid material. The particles or plurality of interconnected particles are useful for medical, dental or veterinary or biotechnical applications, such as bone, tooth or skin implants, including alveolar ridge augmentation, or as a growth substrate material. Any biocompatible material can be used, including ceramics such a hydroxylapatite.

51 Claims, 3 Drawing Sheets

OTHER PUBLICATIONS

Kenneth E. Salyer, "Interpore 200 Porous Hydroxyapatite as an Onlay Graft in Maxillofacial Surgery," Interim Report, 1985.

"Interpore 200 Porous Hydroxyapatite," 1984 Interpore International.

"Interpore 200 Biomatrix Granules".

Surindar N. Bhaskar, John M. Brady, Lee Getter, Marvin F. Grower and Thomas Driskell, "Biodegradable Ceramic Implants in Bone," Oral Surgery, vol. 32, Aug. 1971, pp. 336-346.

Paul Predecki, J. E. Stephan, B. A. Auslaender, Vert. L. Mooney and K. Kirkland, "Kinetics of Bone Growth into Cylindrical Channels in Aluminum Oxide and Titanium," J. Biomed. Mater. Res., vol. 6, 1972, pp. 375-400.

Jerome J. Klauritter and Allan M. Weinstein, "The Status of Porous Materials to Obtain Direct Skeletal Attachment by Tissue Ingrowth," Acta orthop. belg., 1974, 40, pp. 755-765.

J. D. Bobyn, R. M. Pilliar, H. U. Cameron and G. C. Weatherly, "The Optimum Pore Size for the Fixation of Porous-Surfaced Metal Implants by the Ingrowth of Bone," Clinical Orthopaedics and Related Research, No. 150, Jul.-Aug. 1980, pp. 263-270.

E. Fischer-Brandies and E. Dielert, "The Resorption of the Alveolar Ridge: Possibilities for Treatment and Some Perspectives," Quintessence International, 1985, pp. 827-831.

Ole T. Jensen, "Combined Hydroxylapatite Augmentation and Lip-Switch Vestibuloplasty in the Mandible," Oral Surgery, Oral Medicine, Oral Pathology, vol. 60, No. 4, Oct. 1985, pp. 349-355.

Garth R. Griffiths, "New Hydroxyapatite Ceramic Materials: Potential Use for Bone Induction and Alveolar Ridge Augmentation," The Journal of Prosthetic Dentistry, vol. 53, No. 1, Jan. 1985, pp. 109-114.

Sanford S. Rothstein, Donald Paris and Barbara Sage, "Use of Durapatite for the Rehabilitation of Resorbed Alveolar Ridges," JADA, vol. 109, Oct. 1984, pp. 571-574.

John N. Kent, James H. Quinn, Michael F. Zide, Luis R. Guerra and Phillip J. Boyne, "Alveolar Ridge Augmentation Using Nonresorbable Hydroxylapatite With or Without Autogenous Cancellous Bone," J. Oral Maxillofac. Surg., 41, 1983, pp. 629-642.

Alveolar Ridge Augmentation in Edentulous Patients, vol. 1, Symposium Chairman: Victor J. Matukas (articles by: Terrance A. Rust, Eugene P. Sager and Victor J. Matukas).

"Review of Clinical Experiences," Supp. No. 2, pp. S67-S75.

R. K. Gongloff, "Comparison of Collagen Container and Uncontained Implants of Hydroxylopatite," Journal of Dental Research, vol. 65, Abstracts of papers from Mar. 12-15, 1986 Annual Session of Amer. Assoc. for Dental Research.

Koyama et al., "Cervical Laminoplasty Using Apatie Beads as Implants", Surg. Neurol., 1985, pp. 663-667.

Koyama et al., "Porous Hydroxyapatie Ceramics for Use in Neurosurgical Practice", Surg. Neurol., 1986, pp. 71-73.

"Bone and Teeth from Asahi", Clinica World Medical Device News, No. 157, p. 14, Aug. 2, 1985.

Suda, K. Arch. Jpn. Chir., 1985, pp. 261-264.

Jarcho, Clinical Orthopaedics, No. 157, Jun. 1981, pp. 259-278.

Shima et al., J. Neurosurg., Oct. 1979, pp. 533-538.

Ogiso, Kokubyo Gakkai Zasshi, vol. 49, 1978.

BIOCOMPATIBLE PARTICLES AND CLOTH-LIKE ARTICLE MADE THEREFROM

FIELD OF THE INVENTION

The present invention relates to biocompatible particles and an article incorporating a plurality of such particles, and more particularly, to miniature interconnectable biocompatible particles, their use as dental or bone implants, prosthesis or as in vivo or in vitro growth substrates in biotechnical applications. This invention also relates to the biocompatible particles in a strung, woven, spun, rope, crocheted, braided, nonwoven, web or knitted form.

BACKGROUND OF THE INVENTION

A number of materials are useful in medical, dental, biotechnology or veterinary applications because they are biocompatible in the sense that they do not present a serious rejection reaction when used as a biological implant or prosthesis or as in vivo or in vitro growth substrate. One difficulty with the use of such materials in veterinary, dental or surgical applications involves the fact that many such materials, including ceramics, metals, plastics, and composites, are rigid and hard. In many instances, this necesitates that the prosthesis or implant be shaped by grinding, sawing or otherwise during the surgical procedure in order to assure proper fit. E. Fischer-Brandies, "The Resorption of the Alveolar Ridge", *Quintessence International,* Vol. 12, 1985, 827–831 at 828. Alternatively, it may be necessary to provide a plurality of different sizes and shapes of implants or prostheses so that after surgery has begun, the surgeon can select the proper size and shape to assure the desired fit. These methods in general involve some additional surgical risk and increased costs since the surgical procedure is prolonged during the shaping and/or selection of the implant or prosthesis.

To eliminate the necessity for such shaping or selection, some types of dental or surgical implant or prosthesis procedures have employed a mass of particles in which each particle is typically on the order of a few microns up to a few millimeters in size. One such technique involves combining a mass of ceramic particles with a material which cures or sets to form a hard body, such as a polymerizable bonding material, as described in U.S. Pat. No. 4,097,935 issued July 4, 1978 to Jarcho. This technique, however, may be unacceptable when it is desired to have an implant with an enhanced number of sites available immediately for bone or tissue ingrowth, or when some amount of flexibility of the implant is desired, or when it is desired to minimize or eliminate shrinkage and/or compaction as the bonding material disintegrates or is resorbed. An implanted hard body can, particularly under condition of stress such as caused by mastication, rupture surrounding soft tissue, creating potential infection and bacteria growth sites. The Jarcho patent also discloses increasing the porosity of a sintered non-porous body by drilling or machining holes. The Jarcho patent does not disclose interconnectable or flexibly connected particles.

In other applications, particles are placed in the desired location, without a curable or setting bonding material, and the tissue of the host is allowed to grow into the implant material to eventually provide structural integrity. One such technique is used in alveolar ridge augmentation. In this technique, particles of a ceramic, often hydroxylapatite, can be injected, preferably in blood or saline solution, after suitable surgical preparation, by a syringe. Injection by syringe is possible because the particles are of a fluidizable size, i.e. are sufficiently small that, en masse, they are substantially fluid-like. The fluid-like characteristics of such particles allows not only ease of implantation but also permits the mass of ceramic material to be formed in a desired shape. Unfortunately, the fluid-like character of this material also requires particular care in surgical technique and, even with the best known technique, sometimes results in migration of the particles, i.e. movement to a location other than that desired. Such migration is a particular problem when the implant site is subjected to mechanical stress. Because tissue growth of the host into the implant material takes time, the patient must refrain from stressing the fluid-like implant and, in the case of alveolar ridge augmentation, this often means a soft or liquid diet for an extended period and often, containment with a stent. *Review of Clinical Experiences,* Supplement No. 2 S67 through S75.

As noted above, ceramic particle delivery has been attempted by mixing ceramic particles with saline or blood to form a slurry that will, to some degree, hold its position after placement. Victor J. Matukas "Newer Clinical Applications of Durapatite" at p. 22 in *Alveolar Ridge Augmentation in Edentulous Patients.* Another method which has been used in an attempt to minimize particulate migration is the encapsulation of particles within a tube-like structure as described in R. K. Gongloff "Comparison of Collagen Container and Uncontained Implants of Hydroxylapatite," *Journal of Dental Research,* Vol. 65, p. 336 (abstract only). This method, however, imposes a barrier between the particles and the host tissue relatively impermeable to easy ingrowth of tissue and can result in some retardation of tissue ingrowth into the mass of particles. The surgeon must pack the tube before or during the procedure or must have a variety of packed tubes to enable selection of the proper size. The tube is also subject to rupture with consequent loss of material.

Applications such as alveolar ridge augmentation involve two somewhat competitive considerations, viz., provision of mechanical strength, and provision of ingrowth sites, such as pores between or through the particles. Up to now, the primary means for anchoring implanted particles has been growth around the exterior of the particles. The need for tissue ingrowth into the implant material has prompted development of ceramic particles having a porous structure to provide sites for tissue ingrowth. However, provision of ingrowth sites has, up to now, invariably had a deleterious effect on the strength of the material. The attempt to provide acceptable ingrowth sites is illustrated in U.S. Pat. No. 3,890,107 issued June 17, 1975 to White et al. and 3,929,971 issued Dec. 30, 1975 to Roy, which disclose a ceramic particle constructed so as to have a plurality of pores. Particles with this type of porosity have a typical crushing strength of about 0.8 pounds (0.4 kg) when provided in a 20–25 mesh size. This crushing strength is substantially less than the crushing strength of particles which do not have such a highly macro-porous nature, which are typically on the order of about 5 pounds (2.3 kg) and up to 15 pounds (6.8 kg) or more. Further, the size and shape of the pores formed by this method are determined by the structure of marine life skeletal material which forms a basis for the final form of the particles and thus are limited to whatever forms happen to be found in nature. These materials are not adapted to solve the problem of implant migration.

Another method of providing porosity involves adjustment of reaction conditions during preparation of particles. It is possible to affect total microporosity volume in a ceramic by adjusting processing conditions such as sintering temperature and pressure, as described in U.S. Pat. No. 4,503,157 issued Mar. 5, 1985 to Hatahira. Such methods are ineffective to produce any desired pore shape or size and, further, cannot be used to affect pore characteristics without also affecting other ceramic characteristics such as crystal size. Another method of providing porosity includes tumbling the particles to produce particle agglomeration prior to sintering. It is particularly difficult in this method to adequately control pore size and density.

Accordingly, there is a need for a biocompatible article which can be implanted in tissue which has an amount of moldability or shapability, and yet is not subject to substantial migration from the implantation site or compaction after implantation. There is further a need for a biocompatible article which can be readily molded or formed to the desired size and shape during implantation. Additionally, there is the need for a biocompatible material which has high strength and is resistant to migration from the implant site when subjected to mechanical stress. Also, there is a need for a biocompatible implant material which is amenable to tissue ingrowth but which has a high crushing strength.

SUMMARY OF THE INVENTION

The instant invention comprises a particle, useful for tissue implantation and tissue culturing, which is biocompatible said particle having a means for interconnection with another biocompatible particle.

Another embodiment of the instant invention comprises a biocompatible particle which has at least one aperture or has an interlocking shape.

In another embodiment, the instant invention comprises an apertured ceramic particle having a diameter below about 3000 micrometers (microns).

A further embodiment of the instant invention comprises a web-like article. The web can comprise a sheet or film or can comprise a plurality of strands with each of the strands comprising a plurality of biocompatible apertured particles with each particle located on a filament which passes through an aperture of each of the particles. A plurality of connective filaments interconnects these strands.

In a further embodiment the instant invention comprises a process for producing a web-like ceramic article. The process comprises providing a plurality of apertured ceramic particles with a diameter less than about 3 millimeters (mm). A flexible material is passed through the aperture of each of the particles to form a strand of ceramic particles. This strand of ceramic particles is then formed into a web-like or rope-like ceramic article.

Another embodiment of the instant invention comprises a method for biological tissue implantation. This method involves implanting a plurality of biocompatible ceramic particles having a diameter less than about 3 mm and having a crushing strength of at least about 4 pounds.

DETAILED DESCRIPTION

Figure 1:
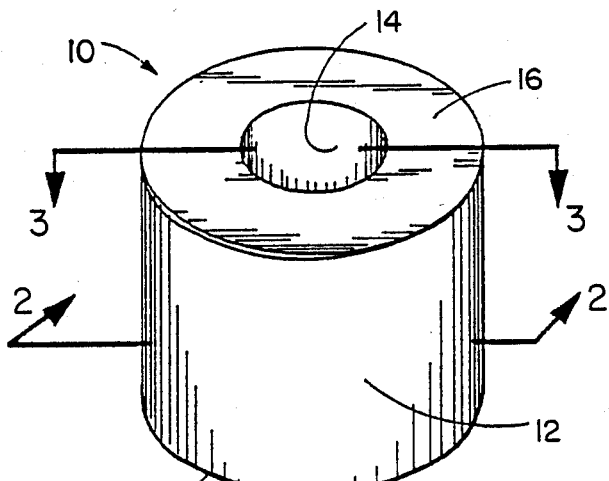
FIG. 1 is a perspective view of a single apertured particle.

The present invention involves providing biocompatible material for use as implants, or growth substrates or other medical, dental or biotechnical applications. The material can be in a flexible form so that the material can be readily shaped for the required medical, dental, veterinary, biotechnology or tissue growth use. The invention includes particles having means for interconnection and also include a plurality of interconnected particles, whether or not the particles have means for interconnection.

In one embodiment, the material can be in the form of particles having a means for interconnecting the particles, i.e. restricting the movement of particles relative to each other so as to control migration of particles to sites other than those desired. The means for interconnecting the particles includes apertures through the particles (through which an interconnecting medium can be passed or placed) and interlocking external shapes of the particles. Thus, according to this invention, particles are provided which are adapted to interconnection with one another. It should be emphasized that, though the particles have a means for interconnection, there are uses for such particles even when such interconnection is not used. For example, apertured particles are adapted for interconnection because the apertures can be employed to interconnect the particles by stringing, knitting, incorporation in a composite, and other means described more fully below. However, even when such interconnection is not used, particles having a means for interconnection are useful because the apertures provide useful and controllable tissue ingrowth sites, and particularly can be used to provide tissue implantation sites without seriously compromising the strength of the particles as compared to particles without interconnection means including porous particles.

The invention also includes a plurality of interconnected particles, regardless of whether all, some or no such particles have a means for interconnection. Interconnection can be by dispersion in, adhesion to or entrapment in a web. The web can include a film or sheet such as a polymer film, a randomly connected plurality of fibers such as a felt or nonwoven fabric or an ordered connection of fibers, filaments or strands such as a woven, crocheted, braided, spun, or knitted web. Interconnection can be in the form of a string or rope. Interconnection can also be accomplished by dispersion of the particles in a shape or plug of flexible material such as a polymer. When the particles have means for interconnecting, interconnection can be by dispersion in a rigid material such as a curable resin material. The particles can be surrounded or enveloped by a sock of material, preferably permeable to tissue ingrowth.

The individual particles and interconnected plurality of particles of the present invention provide a number of advantages. The particles possess high crushing strength, comparable to that formerly obtained only in non-porous, non-apertured particles, and provide an aperture of a desired size to obtain the desired degree, penetration, speed, and type of tissue ingrowth. By providing both an outer surface and an inner surface, the particles produce additional sites for tissue ingrowth and provide the possibility for tissue to grow through the particle to provide a stronger mass and to lessen the tendency to migrate, as compared to previous dense particulates. The web-like or cloth-like ceramic article provides stability against migration of ceramic particles, and the ability to shape, cut and suture, thus providing for adaptation of the material to the implant site prior to and during surgery.

The particles of the present invention are made of a biocompatible material because the particles are intended for a veterinary, biotechnical, dental, or medical use, such as bone or tooth implantation or prosthesis. As used herein, "biocompatible" means substantially free from deleterious effects on living systems particularly with regard to the intended use. In surgery or implant contexts "biocompatible" means substantially free from inducing a serious rejection reaction. A number of biocompatible materials can be used in the present invention including calcium phosphate ceramic materials such as hydroxylapatite, tricalcium phosphate such as whitlockite (beta form), calcium pyrophosphate, octacalcium phosphate, calcium fluorapatite, tetracalcium phosphate, other ceramic materials such as calcium carbonate, calcium sulfate, alumina, zirconia, biocompatible glass, e.g. calcium phosphate glass, vitreous and pyrolytic carbons, metals such as stainless steel, tantalum and tantalum alloys, titanium and titanium alloys, and cobalt-chromium alloys, resinous polymers such as polymethylmethacrylate, polyethylene, polypropylene, polyurethane, polylactide (poly-lactic acid), polyglycolide (poly-glycolic acid), dacron, nylon, delrin, collagen, mixtures of the above or similar implantable materials. As used herein, "resinous polymer" includes any polymer which is solid at room temperature. The preferred biocompatible material is a ceramic material, more preferably a calcium phosphate material and most preferably hydroxylapatite.

One aspect of the present invention involves providing an apertured ceramic or biocompatible particle in a substantially cylindrical shape having a diameter less than about 3 millimeter. By "apertured" is meant that the particles have at least one hole or passageway mechanically formed to extend through the body of the particle. The preferred apertured particle is in a shape like a bead or torus.

The apertures are mechanically formed in the sense that they are produced by a mechanical process such as dry pressing, extrusion, casting, isostatic pressing, or formation around a removable material without drilling or machining after the sintering process. The particles are produced in such a way as to provide the desired characteristics normally associated with the respective ceramic or biocompatible materials, such as biocompatibility, thermal and chemical stability, thermal and electrical insulative properties, strength, etc. The apertured particle has superior strength characteristics compared to conventional porous particles. For example, a particle formed according to this invention out of hydroxylapatite has a crushing strength greater than about 1 pound (0.45 kg) and generally between about 4 pounds (1.8 kg) and about 18 pounds (8.2 kg). The crushing strength of an individual particle varies somewhat depending upon the orientation of the particle. The crushing strength of a hydroxylapatite particle when subjected to pressure directed substantially perpendicular to the longitudinal cylindrical axis is approximately 4.6 pounds (2.1 kg). The crushing strength with respect to a force applied substantially parallel to the longitudinal cylindrical axis is about 17.4 pounds (7.9 kg). Thus, the crushing strength of an individual particle is directional. The effective crushing strength of a plurality of particles which are randomly oriented will lie somewhere between the perpendicular and parallel crushing strengths, i.e. between about 4 pounds (1.8 kg) and about 18 pounds (8.2 kg). When a plurality of particles are non-randomly oriented, in the manner described below, the mass of particles will possess a degree of directionality of crushing strength. Thus, the particles can be provided so as to have the greatest strength in the direction of anticipated greatest stress. Aperture orientation can also be arranged to maximize speed of ingrowth which, in turn, enhances strength.

The particular values of crushing strength will vary depending upon the material used to form the particles. Regardless of the biocompatible material used, the particle of this invention possesses superior crushing strength with respect to conventional porous particles of the same material and possesses directionality of crushing strength compared to conventional porous or nonporous biocompatible particles of comparable material.

The preferred biocompatible particle comprises ceramic material which is dense, having more than about 90 percent of its theoretical density, preferably more than about 95 percent, and more preferably more than about 98 percent of its theoretical density. Determination of density in this context presents problems both of definition and of measurement. These problems relate to the fact that the density of a material is affected by the scale on which density is determined. For example, if the scale is such that an intentionally formed aperture in the particle is included in the mass and volume on which density is based, a lower value for density will result than if the scale is substantially less than the size of the intentionally formed aperture so that the volume and mass of the aperture can be excluded from the density determination. Unless this scale is defined, density values in this context have little meaning. As used herein, unless otherwise noted, density of individual particles is determined on a scale such that intentionally formed apertures are not included in the mass or volume on which density determination is based.

One advantage of the invention is the ability to control the density of a mass of the particles by controlling the size of the apertures or pores relative to the size of the particles. The density can further be controlled by forming the particles in a desired shape so as to determine the average inter-particle volume and shape. The theoretical density of the ceramic material will vary depending upon its composition. The theoretical density of pure hydroxylapatite is about 3.15 grams per cubic centimeter. The tap density of the bulk hydroxylapatite particulate of this invention is approximately 1.83 grams per cubic centimeter, but will vary depending on particle shape and size distribution, in a manner well known in the art. Tap density includes the mass and volume of intentionally formed apertures and interparticle spaces.

A number of medical workers have conducted research into the optimal pore size for bone or tooth implant material. As an example, some workers have found that a pore size of at least 40 to 100 microns is needed to obtain osteoid growth. Other work has indicated that proper ingrowth of mineralized bone requires a pore size of at least about 100 microns, preferably at least about 150 microns, and most preferably at least about 200 microns. An advantage of the particle of the present invention is that the size of the aperture can be positively determined during production, by using the production methods described below, in order to achieve a desired result. Thus, assuming validity of the above size parameters, when the particles of the present invention are intended for an application in which mineralized bone ingrowth is desired, particles can be formed with an aperture diameter greater than 100 microns, preferably greater than 200 microns. If it were desired, for some reason, to obtain osteoid ingrowth without significant mineralized bone ingrowth, aperture diameter could be restricted to below 100 microns. Similarly, if it were desired to obtain fiberous ingrowth without allowing for osteoid growth, particles could be configured with an aperture having a diameter of about 5 to 15 microns. Further, some workers have found that the speed of tissue ingrowth and/or the degree of penetration of tissue ingrowth is related to pore size. In general, the rate of growth has been found to increase with increasing pore size, at least up to a pore size of about 100 microns. Thus, according to this invention, the aperture of the particles and the overall particle size can be selected so as to control the type, speed, or degree of penetration of tissue ingrowth. Further, the aperture of the particles can be selected to provide a desired degree of strength or a desired directionality of strength. In general, load bearing applications require provision of smaller apertures and larger outside diameters, relative to non-load bearing applications. In the case of resorbable components, because resorption is related to the surface area of the particle, the aperture size, shape and number can be selected to provide a desired rate of dissolution.

The present invention, besides providing for control of the aperture size, also allows for controlling the shape, number, and distribution of apertures. According to this invention, apertures can be provided which have a cross-section other than circular such as oval, square, triangular, hexagonal, etc., or which in their longitudinal extent are bent or curved. The aperture is preferably of a size and shape adapted to allow a filament to pass therethrough, i.e. of a diameter large enough to allow passage of such filament, preferably a suture material, and not so curved or bent as to substantially impede insertion or passage of a filament therethrough. More than one aperture can be provided and the apertures can be configured so as to intersect, or so as to be discrete, as desired. In contrast, previous processes for production of small ceramic particles depended upon chemical, biological, sintering or physical (e.g. agglomeration) processes for affecting pore shape, number and distinction.

The preferred ceramic material for production of the particles are hydroxylapatite and tricalcium phosphate or mixtures thereof. Hydroxylapatite is particularly useful for non-resorbable applications, such as alveolar ridge augmentation, treatment of bone cyst sites, or other bone defects such as those due to disease, trauma or inherited abnormalities. Hydroxylapatite is particularly biocompatible, is radio-opaque and can be formed into a high density, high purity, polycrystalline particulate form. Tricalcium phosphate is useful in resorbable applications, for example, for periodontal defects in which bone subsequently ingrows and provides support. Other types of ceramic materials which can be used in this invention include $Al_2O_3$, $ZrO_2$, calcium pyrophosphate, octacalcium phosphate, calcium fluorapatite, tetracalcium phosphate, calcium carbonate, carbonates such as SiC, nitrides such as SiN, glasses, e.g. calcium phosphate glass or "bioglass", vitreous or pyrolytic carbon, other implantable ceramic materials and/or mixtures of the above. It is also possible to use non-ceramic material for formation of apertured particles, such as polypropylene, polyurethane, polymethylmethacrylate, polyethylene, CoCr alloys, titanium and titanium alloys, tantalum and tantalum alloys, polylactide polymers, polyglycolide polymers, dacron, nylon, delrin, natural, prepared or modified collagen, and others, or a combination of the above non-ceramic materials with other non-ceramic materials or with ceramic materials or a mixture of particles having one composition with particles having another composition.

The preferred particle shape is that of a cylindrical shell defined by two coaxial cylindrical surfaces. Referring now to FIG. 1, the preferred particle 10 comprises a generally cylindrical form 12 having an aperture 14 extending therethrough. The particle has a length defined by the distance between an upper surface 16 and a lower surface 18 of the particle. The length is less than about 3 millimeters, preferably between about 225 and 2000 microns, more preferably between about 300 and 1000 microns, and most preferably about 700 microns. The diameter of the particle, i.e. the diameter of the outer cylindrical wall of the particle is less than about 3 millimeters and preferably between about 425 and 2000 microns, more preferably between about 500 and 1000 microns, and most preferably about 925 microns. The cylindrical particle can have a length which is greater than, equal to or less than the diameter of the particle. The ratio of the length to the outside diameter is preferably between about 0.5 and 1.5 and more preferably is about 0.75. The particles will thus generally fall in the range of −18 to +40 mesh size. Particles which are in this size range possess certain fluid-like properties, and in particular a mass of such particles can be flowed or injected to a desired position and can be conformed to a desired shape.

The aperture 14 of the preferred particle is defined by a cylindrical surface substantially coaxial with the outer cylindrical surface of the particle. The aperture 14 preferably extends from the top surface 16 to the bottom surface 18 of the particle. The aperture 14 can be between about 500 and 1000 microns or more. The aperture 14 is preferably less than about 500 microns in diameter, more preferably between 150 and 400 microns in diameter, most preferably about 225 to 300 microns in diameter.

The above-described range of sizes for the preferred particle relate to particles intended for use in alveolar ridge augmentation. The dimension, shape, and other characteristics of the particles within the scope of this invention may deviate from the above-described preferred size and shape, e.g. in some applications in which particles are intended for uses other than alveolar ridge augmentation.

The particles of the present invention can be formed by a number of methods. The preferred method of formation of ceramic particles is die pressing. The ceramic is formed into substantially dry particles of a size small enough to be easily placed in the die. The particles are mixed with binders, release agents, and other additives normal to die pressing methods and introduced into a die having the required size and shape to produce a green body which can be sintered to the desired final product size and shape. The mixture is placed in the die and pressed to produce a green body which can be handled. The green body is removed from the die and sintered to produce the final sintered particle.

In a preferred method which uses hydroxylapatite, a feed material is produced from a slurry as described by Newesley and Hayek, in *Organic Synthesis,* Volume 6, 1963. This slurry can be mixed with additives useful as binders, plasticizers, release agents, deflocculants, and so forth. Such additives can include polyethylene glycol, Carbowax 8000, polyvinyl alcohol, cellulose derivatives, calcium stearate, stearic acid, oleic acid or water. The slurry can be spray-dried to produce a fine particulate matter which is free-flowing and will readily fill a die cavity. In order to assure a flowable character, the particulate material is preferably less than about 100 microns in diameter and is preferably dried, e.g. to minimize particle agglomeration. This dry particulate comprising powdered hydroxylapatite is next mechanically compressed into a shaped body by placing the particulate into a die cavity. The die cavity has a mandrel or core rod which forms the aperture in the finished product. The green body is somewhat larger than the desired final size, to allow for shrinkage which will occur during subsequent sintering. The die cavity thus has a diameter such that the produced green body will, upon sintering, shrink to a size less than 3 mm in diameter. The die cavity is preferably less than 1.5 mm in diameter. Sufficient pressure is applied to the filled cavity to produce a green body which can be handled and effectively sintered and having a final desired shape. The amount of pressure used depends on the density desired for the green body, the amount of sintering shrinkage that can be tolerated and other factors known in the art. Pressing is preferably accomplished using a pressure of at least about 69 MPa (about 10,000 psi). An anvil style press can be used, preferably with a rapid stroke rate such as 90 strokes per minute or faster. An opposed action punch can be used to provide high green densities.

If it is desired to round the edges of the particles, the particles can be rolled in a tumbler or ball mill. If sufficient particles are present, media is not required. The rounded green particles are washed and dried before sintering. Alternatively, rounding can be accomplished by milling after sintering has been accomplished, although a longer milling time would be required.

The green body is removed from the die or the mill and sintered under conditions of temperature, pressure, time, and atmosphere selected to accomplish at least about 90 percent densification. The green bodies are preferably bisqued prior to sintering. A 3 hour ramp to about 1000° C. with a 1 hour bisque time is operable. When a large amount of ceramic is processed, a 100° C. per hour heating to a 300° C., 1 hour soak followed by a 3 hour ramp to a 1000° C., 1 hour soak can be used. Sintering is preferably conducted at approximately 1000°–1200° C. with a soak time of about 0.1 to 10 hours.

When materials other than hydroxylapatite are used, the particulars of the dry pressing method, such as the additives used, the die pressure, sintering temperature and atmosphere, densification aids and soak time, are varied to accommodate the characteristics of the ceramic or other materials. Die pressing can produce particles which are substantially uniform in size, shape, porosity, density and other physical characteristics.

Other methods of producing the ceramic particle of this invention include extrusion, casting, isostatic pressing, hot pressing and injection molding. It is also possible to deposit the desired material onto a decomposable substrate which will leave behind the desired configuration. Further, it is possible to produce a configuration which could be cut or broken into the desired configuration such as by soaking in water. A configuration in the shape of tubing can be sectioned or broken into the desired particle size and shape. Cutting can be accomplished before heating, after bisque sintering or after full sintering.

According to one method, the hydroxylapatite slurry produced as described above by the method of Newesley and Hayek can be treated such as by partial drying to place in an extrudable form. The extrudable slurry of hydroxylapatite ceramic precursor material can be extruded in a tube-like form and the tube-like form can be sectioned into cylindrical shell-shaped objects, either before or after a bisque or a final sinter heating.

Non-ceramic particles can be formed in a number of manners including pressing, casting, stamping, injection molding, powder compaction and extrusion. The method of choice depends upon the shape of the particle and the material being used.

Another aspect of this invention involves biocompatible particles whose means for interconnection includes providing the particles with an external shape which results in a degree of self-interlocking among particles and also includes providing a plurality of such particles. This aspect of the invention also includes a plurality of biocompatible particles having an interlocking shape substantially all of which are interconnected with at least one other particle. In this respect, the biocompatible particles of this invention can be produced in a shape other than cylindrical. In particular, particles, whether apertured or not, can be produced in a shape configured to produce a degree of interlocking between the individual particles. Such interlocking is useful when it is desired to reduce the amount of particle migration, as when the particles are used as a biological implant. On the macro scale, the effect of such interlocking shape is to increase the apparent viscosity of a mass of the particles.

A number of shapes of particles can be used to produce this self-interlocking, including a crescent or C-shape, a horseshoe shape, fishhook shape, an S-shape, an L-shape, a star shape or similar forms. In applications where it is desired to inject the particles by syringe, interlocking particles can be provided prior to implanting in "binary" form, i.e. in two or more distinct forms which do not interlock with themselves but will interlock upon contact with other forms.

As with the apertured particles, the interlocking particles can be formed of a number of biocompatible materials including ceramics, metals, polymers, or organic materials. The method of production of the interlocking particles includes die pressing, extrusion, isostatic pressing, hot pressing, and casting. Ceramic particles are preferably formed by a die pressing method, somewhat analagous to the method described above with respect to the apertured particles. In the case of interlocking particles, however, it may or may not be necessary to provide a mandrel in the die press cavity such as that used to form apertures in die pressed apertured particles.

A further aspect of this invention includes providing a plurality of biocompatible particles in interconnected form. The plurality of particles can be interconnected by a flexible medium or, at when least some particles have means for interconnecting, the particles can be interconnected by a substantially rigid medium. The plurality of biocompatible particles with means for interconnecting can be provided in substantially non-moldable form by providing a plurality of particles which are interconnected by a rigid medium, for example, a resin-type medium such as polymethyleethacrylate or a non-resinous material such as plaster. In this embodiment, the biocompatible particles can be immersed in a fluid or flexible medium which is capable of being hardened by exposure to or mixture with a second material such as a catalyst or reactant in the manner of "epoxy" adhesive. Such a method can be practiced by hardening the mass into a shape which is predetermined before surgery to properly fit into the surgical implant site. Alternatively, the plurality of particles can be dispersed in a hardenable material which can be positioned in the implant site and properly shaped prior to hardening in place.

Whether an interconnecting material is "flexible" or "rigid" depends partly upon the application for which the interconnected plurality of particles is intended. As used herein, a "flexible" material generally refers to a material which can be deformed with some degree of inelasticity so that the plurality of particles interconnected by such medium is substantially moldable so as to conform to a desired contour. For example, when an article comprising a plurality of interconnected particles is to be used for alveolar ridge augmentation, the article is moldable if the article can be inelastically deformed using ordinary pressure, for example digital pressure by the surgeon, to conform the article to the contour of the existing alveolar ridge so as to lie in intimate contact therewith. If the article is to be used for, for example, building an augmentation layer on a traumatized cheek bone, a somewhat lesser degree of inelastic deformability is required in a moldable article since the cheek bone is typically somewhat less curved than the alveolar ridge. In this sense, a non-moldable article is an article which cannot be inelastically deformed to a desired contour under, e.g. ordinary operating room conditions and thus must either be cast to the desired shape, or must be reshaped such as by grinding or sawing to form to the desired contour.

When the particles are interconnected by a flexible medium, the plurality of particles preferably comprises at least one particle with a particle diameter less than about 3 millimeters said plurality of particles preferably being between about +18 and −40 mesh in size. The plurality of particles is preferably used in association with a flexible material interconnecting each of said biocompatible particles to at least one other of said particles. In this manner, there can be provided a mass of particles which possesses properties of the underlying particle substance such as the hardness, chemical and thermal stability of ceramics, metals, or plastics, but which also possesses a degree of moldability, and can thus be shaped and/or sutured in a manner not possible with hard rigid material like metal or ceramic which is in ordinary form. Such moldable articles can also be used to provide for orientation of particle apertures, when present, to impart desired tissue ingrowth capability and for directionality of crushing strength, as described above. The moldable article can be provided in the form of a sheet or web-like material or can be provided in the shape of a moldable block or plug of biocompatible particles interconnected by a flexible medium.

Another aspect of the instant invention comprises a plurality of flexibly interconnected biocompatible particles. The biocompatible particles can comprise any of the ceramic, metallic, polymeric, organic or other materials disclosed herein as being useful for this invention.

A web-like article can be produced by stringing, knitting, weaving, crocheting, spinning, braiding, rope making and like processes. The web-like article can also be produced by adhering particles to a flexible web or sheet. In the preferred process, a plurality of apertured ceramic particles having a diameter less than about 3 millimeters are strung onto a flexible material, reminiscent of a string of beads. Such stringing can be accomplished by hand, possibly assisted by trays or other devices for orienting the apertures to provide for ease of stringing. Stringing can also be accomplished mechanically by a bead stringing machine. The string of ceramic particles can be treated to prevent unstringing in the event the flexible material is cut or broken. Such treatment can include knotting, looping, use of a plurality of strands of flexible material, hat treatment, chemical reaction, introduction of an adhesive material, and other similar processes.

The flexible material used to string the beads is any material or combination of materials capable of being passed through the aperture of the particle, and preferably is in the form of a filament, thread, or yarn material, and is also preferably biocompatible. The flexible material preferably has a flexibility and tensile strength comparable to suture materials and may in fact comprise suture material. A number of stringing materials are usable, including, but not limited to, resorbable sutures of gut, chromic gut, and other collagen based materials, polyglycolic acid, polylactic acid, polydioxanone, and polygalactic acid. Non-resorbable stringing materials can include silk, nylon, polyethylene, stainless steel, tantalum and tantalum alloys, titanium, titanium alloys, CoCr alloys, polypropylene, polyurethane, polymethylmethacrylate, polylactide polymers, dacron, delrin, and the like or mixtures or combinations thereof.

Figure 4:
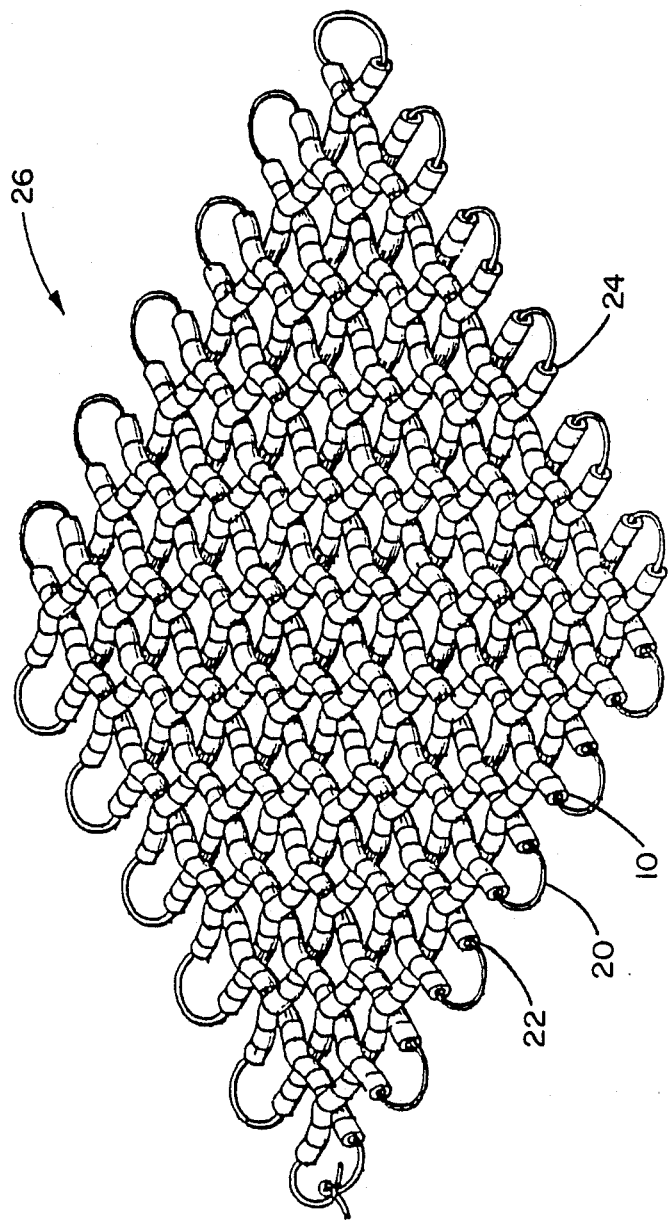
FIG. 4 is a perspective view of a woven article comprising a plurality of apertured particles strung on strands.

The strand-like ceramic article can be further used to provide the strand article in the form of a web or to produce a web-like or cloth-like ceramic article by such methods as knitting, weaving, crocheting, braiding, or fabricating a rope or non-woven web. The ceramic beads can be incorporated into a woven article by passing either or both the warp and weft threads, filaments or yarns through the ceramic particles. One method of accomplishing this is to provide warp and weft filaments which are both beaded with ceramic particles. One product which can be made by such method is depicted in FIG. 4. In the depicted embodiment, a plurality of apertured particles 10 are strung on fibers 20. The strung particles comprise both the warp 20 and weft 24 strands of a cloth-like material 26. It should be understood that the cloth-like material 26 depicted in FIG. 4 is but one embodiment of a woven article in which both warp and weft threads are beaded with ceramic particles. Other woven articles, according to this invention, can be provided having a different style of weave. Another method of producing a woven article is to interconnect beaded strands with a material such as a tape yarn or a second filament, e.g. by aligning the bead particles on the warp strands so that weft filaments can be passed through the particle apertures. A third method is to provide each ceramic particle with two apertures, one for warp filaments and another for weft filaments. The cloth-like article preferably is formed in such a way that it can be cut or otherwise shaped without substantial unraveling or loss of ceramic material. The tightness of knitting or weaving can be adjusted in order to control the bulk density of the cloth-like material as well as its degree of moldability. A relatively rigid article, which is nevertheless cutable and suturable, can be provided using a tight weave or knit. The cloth-like material can comprise a single layer of ceramic particles or can be in the form of multiple layers of ceramic particles. A multiple-layer article can be formed by adhering a number of separately-formed single layer ceramic articles, such as by use of an adhesive material, sewing, suturing, tying, or the like, or can be woven or knitted in a single multi-layer article.

Figure 5:
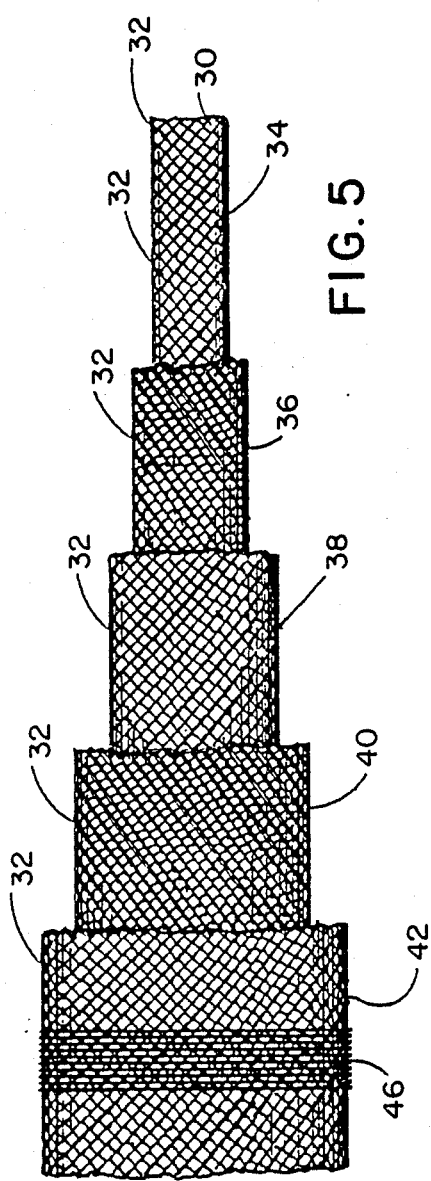
FIG. 5 is an elevational view of a rope-like article comprising a plurality of helically oriented strands of interconnected particles, with each layer extending beyond the termination of the next-most exterior layer.

A specific embodiment of a rope-like article produced according to this invention is depicted in FIG. 5. A plurality of interconnectable particles 30 are interconnected in a linear fashion to form a plurality of strands 32. Six such strands are twisted together in helical fashion to form a core 34 having a right-handed helical orientation. A second group of strands 32 is twisted about the core 34 in a left-handed helical fashion to form a first covering layer 36. A second plurality of strands 32 is twisted around the first covering 36 in right-handed helical fashion to form a second covering 38. A third plurality of strands 32 is twisted around the third covering 38 in left-handed helical fashion to form a fourth covering 40. A fifth plurality of strands 32 is twisted about the fourth covering 40 in right-handed helical fashion to form a fourth covering 42. The end of the rope-like article is bound by a number of turns of suture material 46 to prevent unraveling. Although the core portion 34 and first, second and third coverings 36, 38, 40 are shown projecting from the end of the first, second, third and fourth coverings 36, 38, 40, 42 respectively, for clarity of illustration, the coverings 42, 40, 38, 36 and core 34 are preferably co-terminous to provide a blunt-ended rope-like article. The number of strands in the core 34 and coverings 36, 38, 40, 42 can be varied and the angle and orientation of the helical strands can be varied to produce rope-like articles having a number of different diameters. A number of rope-like articles can be themselves twisted together in a helical fashion in manner well known in the rope-making art. The rope can be produced in a variety of lengths and preferably is produced in 25 to 100 mm lengths and 4 to 12 mm diameters.

Figure 6:
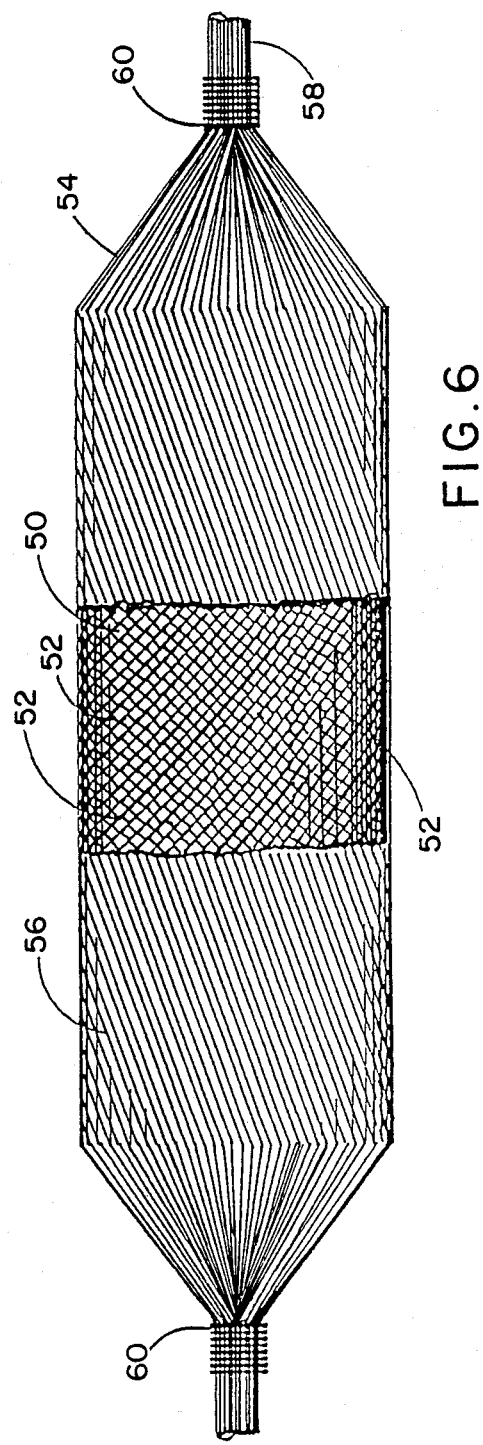
FIG. 6 is an elevational view of a plurality of particles encased in a sock structure with a portion of the sock cut away to show the particles.

Biocompatible particles according to this invention can be provided in combination with an external containment structure or "sock". One embodiment of the so structure is depicted in FIG. 6, having a portion of sock cut away to show the particles contained therein. The particles 50 can have means for interconnecting or can be without means for interconnecting. In the embodiment depicted in FIG. 6, a number of biocompatible particles 50 having means for interconnection are interconnected in a linear fashion to form beaded strands 52. The strands 52 are twisted into a helical configuration.

A generally cylindrical sock 54 is placed exterior to the helically twisted strands 52 to form a sock or sausage-like structure. The sock 54 is formed of one or more helically wound filaments of suture material 56. The ends 58 of the suture material 56 are drawn together and surrounded by several turns of another strand of suture material 60 to prevent unraveling. The sock 54 can be provided by wrapping a number of turns of suture material 56 in helical fashion as shown, or can be woven, knitted, or otherwise formed such as by providing a polymer or collagen tube to provide a sock or casing which preferably has spaces or openings to be easily permeable to tissue ingrowth. The biocompatible particles 50 need not be provided in twisted helical fashion, and, for example, can be provided with the strands in substantially linear relation to each other. Further, the biocompatible particles 50 need not be interconnected but can be packed in the sock or casing structure 54 in a random fashion, provided the sock 54 is sufficiently tightly woven to prevent escape of significant amounts of biocompatible particles 50, preferably having sufficient looseness of weave or knit to allow for desired tissue ingrowth through the sock 54 and around or through the biocompatible particles 50.

Figure 2:
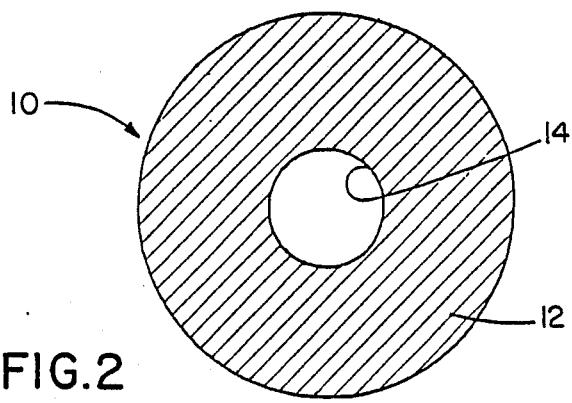
FIG. 2 is a horizontal cross-section of the particle of FIG. 1 taken along line 2—2.
Figure 3:
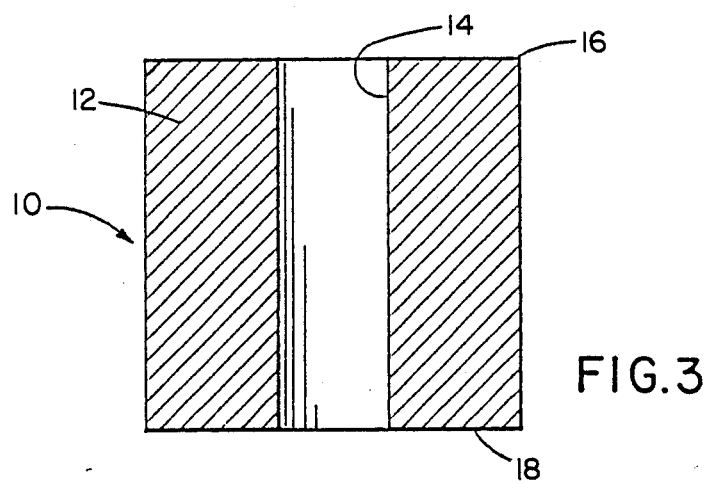
FIG. 3 is a vertical cross-section of the particle of FIG. 1 taken along line 3—3.

The particles which are useful for production of the web-like, cloth-like, rope-like or sock article can be generally any particle comprising a biocompatible material as defined herein and specifically including particles in the form of the apertured ceramic particle described in connection with FIGS. 1 through 3 above. The aperture 14 can be configured to produce not only the desired tissue ingrowth and strength characteristics, but also to facilitate stringing, such as by having a size sufficient to accommodate the desired flexible material as well as a needle or other device used in the stringing process. The particular weaving, knitting, or other process used, may require the provision of multiple apertures in each ceramic particle, such as when one aperture is employed for the warp filament and another aperture is employed for the weft filament.

The web-like or cloth-like article of this invention can be produced using biocompatible particles other than ceramic particles, such as metals, polymers and reconstituted collagen or bone-like material.

Another method of producing a web-like ceramic or biocompatible article involves incorporation of particles into an interconnecting material, e.g. a flexible material such as a sheet-like polymeric, or collagen-type material, a web of non-woven fibers, or a woven fabric. Incorporation can be by adhesion to an adhesive substance, encapsulation of the particle in the interconnecting material, or entrapment among the fibers of an interconnecting material. When the ceramic or biocompatible material is in the form of apertured ceramic particles such as that described above in connection with FIGS. 1 through 3, the interconnecting material can permeate the apertures, locking the particles into place. The pore thus can allow for the use of lesser amounts of interconnecting material between particles than would be necessary to hold in place unapertured particles. Further, the interconnecting material can be a resorbable material that the apertures, following resorption, are available for tissue ingrowth.

The biocompatible article can be formed by applying a layer of particles to flexible material, such as a woven or non-woven web or sheet of polymeric or collagen material. The particles can have means for interconnecting, such as apertures or an interlocking shape, or can be without means for interconnecting. The flexible material is preferably biocompatible and can comprise a resorbable material. Application of the particles can be by doctoring, spraying, diffusion of secondary materials into the mass of particles, and the like. The layer of particles can be adhered to the web or sheet by heat bonding, chemical bonding, liquid infusion, mechanical interlocking, or pressure bonding, such as by calendar rolling.

A primary application of both the particles having a means for interconnection and the plurality of interconnected particles is for animal or human bone structure augmentation, such as alveolar ridge augmentation treatment of bone defects caused by trauma or disease or cartilage or skin augmentation, repair or treatment. The moldable article conforms to the surface of the implant site and maintains the ceramic particles in place while tissues anchor the particles through ingrowth during resorption of the resorbable flexible material and sutures. The article can be shaped by the surgeon as desired such as by rolling a sheet to produce a desired diameter, cutting, layering, and the like. With respect to use of the apertured ceramic particle which is not incorporated into a cloth-like article, the particles can be used for alveolar ridge augmentation using procedures well known for hydroxylapatite particle alveolar ridge augmentation, such as procedures described in Victor J. Matukas, *Alveolar Ridge Augmentation in Edentulous Patients,* John M. Kent et al., "Alveolar Ridge Augmentation Using Non-resorbable Hydroxylapatite With or Without Autogenous Cancellous Bone"; Journal Oral Maxillofacial Surgery, 41:629–624, 1983; Sanford S. Rothstein et al., "Use of Durapatite for the Rehabilitation of Resorbed Alveolar Ridges", *Journal American Dental Association,* Volume 109, 571–574, October 1984; Garth R. Griffiths, "New Hydroxylapatite Ceramic Materials: Potential Use for Bone Induction and Alveolar Ridge Augmentation", Journal of Prosthetic Dentistry, Volume 53, 109–114, January 1985; E. Fischer-Brandies, "The Resorption of the Alveolar Ridge: Possibilities For Treatment and Some Perspectives", *Quintessence International,* Volume 12, 1985, 827–831, all incorporated herein by reference.

The particles having means for interconnecting and the plurality of interconnected particles, including particles in a web-like, cloth-like or, preferably, rope-like article, can be used for a number of animal or human bone, cartilage or skin treatments and procedures. This aspect of the invention includes minimizing migration of biologically implanted particles by implanting a plurality of biocompatible particles having means for interconnecting. The plurality of particles can be interconnected by flexible means or by means of the exterior shape of the particles. When used for alveolar ridge augmentation, the particles can be used by insertion under the periosteum and mucousal membranes and over the edentulous resorbed ridges. The rope can be sutured into place to initially prevent mobility of the form during tissue ingrowth. The rope can be placed by pulling it with suture through tissue tunnels, injecting it through the tunnel with the aid of a syringe, placing it in open incisions, pushing through prepared tunnels, any combination of the above, or any other medically acceptable procedure.

The particles and plurality of interconnected particles are useful in applications other than alveolar ridge augmentation. The particles and plurality of interconnected particles can be used to fill bone defects such as dental, orthopedic, maxillofacial, otological sites, cranial sites, and so forth. The particles and plurality of interconnected particles can also be used for cartilage-type augmentation, where soft tissues ingrowing through the particles will make a semi-rigid mass. Examples are augmentation of cartilage in the nose, ears, rib cage, etc. The web-like or cloth-like material is particularly useful for replacement of cartilage, bone, and skin defects and particularly in a plastic surgery use for correcting deformities. Further, the particles and plurality of interconnected particles, and particularly any apertures therein, could act as carriers for tissue growth factors, further enhancing tissue growth and proliferation. The apertured biocompatible material can be used to provide a channel for nerve growth, particularly when the biocompatible material is provided in a tube-like or hollow fiber form, such as that produced by extrusion, with the aperture provided in such size as to be compatible with nerve growth therethrough. Using this material, severed ends of a nerve can be introduced into opposite ends of the aperture to provide for growth of the nerve ends towards each other for eventual union. In this context, the aperture or portions thereof can be provided with a nerve growth enhancement factor.

The biocompatible particles, whether apertured or not, can function as a carrier of other material, such as tissue growth enhancer, bone morphogenic proteins, nerve growth factors, and the like. When the particles are in apertured form, such materials are conveniently placed in some or all of the apertures of the particles, and particularly so as to stimulate tissue ingrowth, preferably ingrowth through the particle apertures as well as around the exterior of the particles.

The biocompatible particles having means for interconnecting are useful as a cell culture substrate. The particle apertures can be employed not only to provide for stability of the particles against migration in an in vitro environment but also can be used to increase the surface area for cell attachment, to control the type and penetration of cell ingrowth into the growth substrate, and/or to provide growth factors. In particular, the biocompatible particles of this invention are capable of maintaining cell phenotype while forming in multi-layer thicknesses.

The biocompatible material of this invention can be produced in fiber form by an extrusion process. Precursor material, for example ceramic precursor material such as hydroxylapatite precursor, is formed into an extrudable slurry and extruded to form fibers, for example, a 50 micron diameter hydroxylapatite fiber, which can be fired to produce a sintered hydroxylapatite green fiber, preferably having at least about 90 percent theoretical density. Such fibers are useful as bone defect fillers or filler for strengthening composites.

Uses of a material which is moldable, cutable, shapable, and sewable as cloth and yet which has the desirable characteristics of a ceramic material are not limited to dental, veterinary, biotechnology, cell culturing or surgical applications. Such a material is useful in forming protective clothing such as heat or projectile-proof clothing. Such material can be used for heat shield surfacing of tools, aircraft, etc., particularly when the flexible connecting material is also heat-tolerant. Such material can be used to cover or line a complex shape, e.g. prior to sintering the shape.

EXPERIMENTAL

The following examples are provided by way of illustration and not by way of limitation.

EXAMPLE 1

264 g of diammonium phosphate (reagent grade) was put in an 18 liter plastic tank along with 9 liters of deionized water and stirred until clear. 2.5 liters of ammonium hydroxide (reagent grade) was then added and stirring continued for 3 hours.

798 g of calcium nitrate, 4 hydrate (reagent grade) was put in an 18 liter plastic tank along with 5.9 liters of deionized water and stirred until clear. 103 milliliters of ammonium hydroxide (reagent grade) was then added and stirring continued for 30 minutes. After stirring was completed, the calcium nitrate solution was filtered through a quantitative, slow filtration, fine precipitate filter and transferred to an 18 liter plastic reaction tank. Upon completion of the transfer, stirring was initiated in the reaction tank.

Immediately when the 3 hour stirring time for the ammonium phosphate solution was ended, transfer of the solution into the reaction tank began. Transfer was by dripping over a 3 hour period. Stirring in the reaction tank was continued for 21 hours after the transfer was completed.

At the end of stirring in the reaction tank, the hydroxylapatite slurry was allowed to settle to about ⅓ its original volume over a 6 hour period. The clear liquid was decanted off the top, and the slurry was resuspended in water to its original 27.5 liter volume. The settling/decantation was repeated twice more, then the slurry was concentrated in an IEC model Centra-7 centrifuge. The collected cake was a hard paste with a water content of about 85 percent. Its total weight was about 380 grams.

The centrifuged, washed slurry was mixed with approximately 10 weight percent defloculent (Darvan 821A) to obtain a solution with a viscosity of approximately 500 centipoise as measured with a Brookfield viscometer. After thorough mixing for about 15 minutes with a non-metallic paddle stirrer, a binder solution was added to the solution. The binder was polyethylene glycol (Carbowax 8000) mixed with distilled water in a concentration of 30 percent solids. The concentration of binder is 5 percent based on the solids content of the hydroxylapatite slurry. This binder solution was thoroughly mixed with the slurry solution for a minimum of 15 minutes and stored in a sealed container until spray dried.

The slurry was mixed thoroughly before spray drying. It was pumped by a peristaltic pump into the chamber onto the rotary atomizer that was rotating at a speed of 8000 to 12000 rpm. The inlet temperature of the spray dryer was about 180° C. with an outlet temperature of about 110° C. The chamber product of the spray dryer was screened −200 mesh +400 mesh. The powder has a Hall flow rate of approximately 45 seconds, and a bulk density of greater than 0.55 grams per cc, with a mean particle size of typically 55 microns. The screened spray dried powder is blended to form a mixture having a 1% content of a die lubricant which is 50% fuel oil and 50% Mobil Comprex BPO to produce the press feed.

The spray dried hydroxylapatite was compacted in a die in an anvil style press. The die cavity was about 1.17 mm (0.046 inches) outside diameter with a core rod of 0.36 mm (0.014 inches) diameter. The fill ratio was about 3:1. The green density was about 55% of the theoretical density of 3.15 grams per cc.

The parts were placed in high purity alumina crucibles that had been acid cleaned. The parts were heated over a period of three hours to the bisquing temperature of 1000° C. for a sintering time of 1 hour.

The sintering was completed by using a ramp of 3 hours to 1100° C. with an isothermal hold of 8 hours.

A first measure of density of the apertured piece was determined by measuring the outside diameter, thickness, and mass of the piece, then calculating the density by dividing the mass by the volume. This density obtained by this method, which includes the mass and volume of the intentionally-formed aperture, was about 90% of theoretical density.

A second measurement of density was determined by using the pycnometric method similar to ASTM C135. Density determined by this method was greater than about 98% theoretical density.

The strength of the parts was evaluated in two directions, diametrical (perpendicular to the hole) compression or simple compression (parallel to the hole). The testing was performed on a combination tensile/compression testing apparatus using a crosshead speed of 0.35 mm per minute. The parts were placed between two flat anvils with 0.2 mm (0.008 inch) thick layer of polyethylene to accommodate any misalignment. The parts were loaded until fracture and the maximum force to fracture was recorded. A minimum of 10 parts were tested in each direction and an average fracture strength was calculated. Parts with an outside diameter of 800 microns, an aperture of 225 microns and a thickness of 650 microns had an average diametrical compression strength of about 4.6 pounds (2.1 kg) and an average simple compression strength of 17.4 pounds (7.9 kg).

EXAMPLE 2

Apertured particles produced according to the process of Example 1 were strung using gut suture or synthetic suture to produce strands of particles.

EXAMPLE 3

A rope structure is produced by having a core of 4 twisted strands covered by 6 strands twisted in the opposite direction. This is then covered by 12 strands twisted in the opposite direction to produce a twisted rope 6 mm in diameter. These are made in 8 mm diameters by increasing the number of core strands or by using a fourth layer of strands.

EXAMPLE 4

A tube-like structure is made by providing strung apertured particles as described in Example 2. Those strung particles are subsequently held in place by an overweaving of bare suture.

EXAMPLE 5

Particles produced by the process of Example 1 were evaluated for biocompatibility or suitability as tissue culture substrates using fibroblasts and chondrocytes. Particles were cleaned and sterilized for use as microcarriers. Fibroblasts or chondrocytes were suspended in growth medium consisting of Dulbecco's Modified Eagle Medium supplemented with 10% (v/v) horse serum and 1% penicillin, steptomycin, and fungizone. Approximately 100,000 cells were seeded on 500 milligrams of apertured particles in 60 mm×15 mm Petri dishes. Four milliliters of growth medium was added per dish. Cultures were maintained in a carbon dioxide incubator and fed twice weekly. By the end of the second week, particles were covered completely with cells. The cells were formed in multi-layer thicknesses while maintaining their phenotype and increasing in number over a hundred fold.

EXAMPLE 6

Fiber extrusion of hydroxylapatite was carried out with an 80% moisture feed and a stainless steel extrusion die with a 0.13 mm (0.005 inch) outlet. Centrifuged hydroxylapatite slurry with a moisture content of 85% was prepared as described in Example 1. The extrusion feed was prepared by oven drying the centrifuged hydroxylapatite at 110° C. to a pasty consistency. The extrusion die, a cylinder with a feed chamber 7.6 cm (3 inches) long and 12.7 mm (½ inch) in diameter, was fitted into a press with a 1814 kg (4000 pound) capacity. Both the extrusion die and plunger were constructed of stainless steel, with a rubber plunger seal. The outlet of the die was fitted with a modified hypodermic syringe needle, 5.1 mm (0.2 inch) in length with a 0.13 mm (0.005 inch) internal diameter. A 9 cc volume of feed, extruded at a pressure of approximately 9.1 kg (20 pounds), yielded 2 cc of 50 micron diameter hydroxylapatite when fired to 1100° C.

EXAMPLE 7

An apertured particle is produced by extruding a hydroxylapatite slurry to form a tube-like structure having an outside diameter of about 1000 microns and an inside diameter of about 250 microns. The tube-like structure is cut into lengths of about 1000 microns each. The cut lengths are sintered to produce sintered apertured hydroxylapatite particles with a density of at least about 90% theoretical.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A plurality of particles useful for tissue implantation said plurality of particles comprising biocompatible particles each of which is flexibly interconnected to at least one other biocompatible particle.

2. The plurality of particles of claim 1 wherein said particles have apertures.

3. The plurality of particles of claim 1 wherein said particles comprise calcium phosphate.

4. The plurality of particles of claim 3 wherein said particles comprise calcium phosphate selected from the group consisting of hydroxylapatite, tricalcium phosphate and mixtures thereof.

5. The plurality of particles of claim 4 wherein said particles comprise hydroxylapatite.

6. The plurality of particles of claim 4 wherein said particles comprise tricalcium phosphate.

7. The plurality of particles of claim 1 wherein said particles comprise material selected from the group consisting of calcium pyrophosphate, octacalcium phosphate, calcium fluorapatite, tetracalcium phosphate, calcium carbonate, calcium sulfate, alumina, zirconia, calcium phosphate glass, vitreous carbon, pyrolitic carbon, silicon carbide and silicon nitride.

8. The plurality of particles of claim 2 wherein said particles have a single aperture.

9. The plurality of particles of claim 4 wherein said particles have a density greater than about 90 percent of the theoretical density.

10. The plurality of particles of claim 9 wherein said particles have a density greater than about 95 percent of the theoretical density.

11. The plurality of particles of claim 4 wherein said particles have a density greater than about 98 percent of the theoretical density.

12. The plurality of particles of claim 1 wherein said particles have a length less than about 3,000 microns.

13. The plurality of particles of claim 1 wherein said particles have a length less than about 1,000 microns.

14. The plurality of particles of claim 1 wherein said particles have a diameter less than about 3,000 microns.

15. The plurality of particles of claim 1 wherein said particles have a diameter less than about 1,000 microns.

16. The plurality of particles of claim 1 wherein said particles have a length in the range of about 225 microns to about 2,000 microns.

17. The plurality of particles of claim 2 wherein said apertures have a diameter greater than about 425 microns.

18. The plurality of particles of claim 2 wherein said apertures have a diameter less than about 500 microns.

19. The plurality of particles of claim 2 wherein said apertures have a diameter greater than about 150 microns 20. The plurality of particles of claim 1 wherein said particles have a crushing strength of at least 4 pounds.

21. The plurality of particles of claim 2 wherein said particles have a length less than about 3000 microns, have a diameter less than about 3000 microns, have a crushing strength of at least 4 pounds and wherein said apertures have a diameter less than about 500 microns.

22. The plurality of particles of claim 1 wherein said particles have a directional crushing strength.

23. The plurality of particles of claim 1 wherein said particles comprise a biocompatible material selected from the group consisting of a ceramic, a metal, a polymer and a combination thereof.

24. The plurality of particles of claim 23 wherein said metal is selected from the group consisting of cobalt, chromium alloys, titanium, titanium alloys, tantalum and tantalum alloys, and stainless steel.

25. The plurality of particles of claim 23 wherein said polymer is selected from the group consisting of polymethylmethacrylate, polypropylene, polyurethane, polyethylene, polylactide polymers, dacron, collagen, and polyglycolide polymers.

26. A plurality of apertured ceramic particles having a diameter less than about 3,000 microns and means for flexibly connecting said particles.

27. The plurality of particles of claim 26 wherein said particles have a single aperture.

28. The plurality of particles of claim 26 wherein said particles are formed by die pressing.

29. The plurality of particles of claim 26 wherein said particles are formed by extrusion.

30. The plurality of particles of claim 26 wherein said particles are in the shape of a cylindrical shell defined by two coaxial cylindrical surfaces.

31. The plurality of particles of claim 30 wherein said particles have a diameter of less than about 3,000 microns and a length of less than about 3,000 microns.

32. The plurality of particles of claim 26 wherein said apertures have a diameter less than about 500 microns.

33. The plurality of particles of claim 26 wherein said particles have a filament passing through said apertures.

34. The plurality of particles of claim 1 wherein said particles have interlocking shapes.

35. The plurality of particles of claim 34 wherein said shapes are selected form the group consisting of a C-shape, a horseshoe shape, a fishhook shape, an S-shape, an L-shape, and a star shape.

36. The plurality of particles of claim 34 wherein said particles comprise a biocompatible material selected from the group consisting of a metal, a ceramic and a polymer.

37. The plurality of particles of claim 34 wherein said particles comprise calcium phosphate.

38. The plurality of particles of claim 37 wherein said calcium phosphate is selected from the group consisting of hydroxylapatite, triacalcium phosphate, and mixtures thereof.

39. The plurality of particles of claim 38 wherein said particles comprise hydroxylapatide having a density of at least 90 percent of theoretical density.

40. A plurality of biocompatible particles having means for interconnection comprising an interlocking shape.

41. A plurality of interconnected apertured biocompatible particles.

42. A plurality of biocompatible particles which are flexibly interconnected.

43. An article comprising the particles of claim 42 interconnected by a biocompatible flexible connective material.

44. The particles of claim 43 wherein each of said particles has an aperture.

45. The particles of claim 44 wherein said flexible material comprises a filament which passes through the aperture of each of said particles to provide a strand of interconnected particles.

46. An article comprising:
  (a) a plurality of strands, each of which comprises a plurality of biocompatible apertured particles residing on a first filament which passes through the aperture of each of said particles; and
  (b) a material interconnecting said plurality of strands.

47. The article of claim 46 wherein said material interconnecting said plurality of strands comprises a second filament.

48. The article of claim 47 wherein said second filament has a plurality of biocompatible apertured particles residing thereon.

49. An article comprising a plurality of biocompatible particles attached to a web of biocompatible material.

50. A plurality of biocompatible particles having means for interconnecting encased in a sock structure.

51. A substrate for culturing cells comprising a plurality of biocompatible particles having means for interconnecting.

* * * * *